(12) United States Patent
Schiffer

(10) Patent No.: US 8,574,279 B2
(45) Date of Patent: *Nov. 5, 2013

(54) METHODS FOR TREATING PSYCHIATRIC DISORDERS USING LIGHT ENERGY

(71) Applicant: Fredric Schiffer, Wellesley, MA (US)

(72) Inventor: Fredric Schiffer, Wellesley, MA (US)

(73) Assignee: Joulesafe, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/668,469

(22) Filed: Nov. 5, 2012

(65) Prior Publication Data

US 2013/0211183 A1 Aug. 15, 2013

Related U.S. Application Data

(63) Continuation of application No. 13/481,820, filed on May 26, 2012, now Pat. No. 8,303,636, which is a continuation of application No. 12/855,258, filed on Aug. 12, 2010, now abandoned.

(60) Provisional application No. 61/233,318, filed on Aug. 12, 2009.

(51) Int. Cl.
A61N 5/06 (2006.01)

(52) U.S. Cl.
USPC .............................................. 607/89; 128/898

(58) Field of Classification Search
USPC ................................ 128/898; 607/45, 89, 90
See application file for complete search history.

(56) References Cited

U.S. PATENT DOCUMENTS

| | | |
|---|---|---|
| 5,963,294 A | 10/1999 | Schiffer |
| 6,145,983 A | 11/2000 | Schiffer |
| 6,214,035 B1 | 4/2001 | Streeter |
| 6,267,780 B1 | 7/2001 | Streeter |
| 6,273,905 B1 | 8/2001 | Streeter |
| 6,290,714 B1 | 9/2001 | Streeter |
| 6,312,451 B1 | 11/2001 | Streeter |
| 6,537,304 B1 | 3/2003 | Oron |
| 6,918,922 B2 | 7/2005 | Oron |
| 7,303,578 B2 | 12/2007 | De Taboada et al. |
| 7,309,348 B2 | 12/2007 | Streeter et al. |

(Continued)

FOREIGN PATENT DOCUMENTS

JP 2007/259959 10/2007

OTHER PUBLICATIONS

Krutmann et al., "Role of Mitochondria in Photoaging of Human Skin: The Defective Powerhouse Model," *Journal of Investigative dermatology Symposium Proceedings*, 14(1), pp. 44-49 (Aug. 2009).

(Continued)

*Primary Examiner* — Bill Thompson
*Assistant Examiner* — Jeffrey Lipitz
(74) *Attorney, Agent, or Firm* — JWIP & Patent Services, LLC; Jacob G. Weintraub, Esq.

(57) ABSTRACT

Methods for treating psychiatric disorders using light energy are disclosed herein. A method for treating psychiatric disorders using light energy includes determining which hemisphere of the brain requires treatment using lateral visual field stimulation (LVFS) and applying light energy to the hemisphere of the brain to treat the psychiatric disorder other than depression. In an embodiment, light energy may include near infrared light (NIR). The methods of the present disclosure may be used to treat a variety of psychiatric disorders. In an embodiment, the methods may be used to treat a psychiatric disorder co-morbid with depression.

7 Claims, 8 Drawing Sheets

(56) References Cited

U.S. PATENT DOCUMENTS

| | | |
|---|---|---|
| 7,316,922 B2 | 1/2008 | Streeter |
| 7,344,555 B2 | 3/2008 | Anders et al. |
| 7,534,255 B1 | 5/2009 | Streeter et al. |
| 7,575,589 B2 | 8/2009 | De Taboada et al. |
| 7,653,433 B2 | 1/2010 | Lozano et al. |
| 7,695,504 B2 | 4/2010 | Anders et al. |
| 2004/0260367 A1 | 12/2004 | De Taboada et al. |
| 2005/0107851 A1 | 5/2005 | De Taboada et al. |
| 2006/0253177 A1 | 11/2006 | De Taboada et al. |
| 2007/0005115 A1 | 1/2007 | Lozano et al. |
| 2007/0179570 A1 | 8/2007 | De Taboada et al. |
| 2008/0004565 A1 | 1/2008 | Streeter et al. |
| 2008/0070229 A1 | 3/2008 | Streeter |
| 2008/0125836 A1 | 5/2008 | Streeter et al. |
| 2008/0221211 A1 | 9/2008 | Streeter |
| 2008/0262565 A1 | 10/2008 | Bentwich |
| 2009/0005837 A1 | 1/2009 | Olmstead |

OTHER PUBLICATIONS

Piazena et al., "Effects of Infrared-A Irradiation on Skin: Discrepancies in Published Data Highlight the Need for an Exact Consideration of Physical and Photobiological Laws and Appropriate Experimental Settings," *Photochemistry and Photobiology*, 86(3), pp. 687-705 (May-Jun. 2010).

Roach et al., "Model Predictions and Measured Skin Damage Thresholds for 1.54 μm Laser Pulses in Porcine Skin," *Proc. of SPIE*, 5319, pp. 325-334 (Jan. 26-28, 2004).

Schroeder et al., "Prevention of Infrared-A Radiation Mediated Detrimental Effects in Human Skin," *Skin Therapy Letter*, 14(5), pp. 4-5 (Jun. 2009).

Schroeder et al., "Photoprotection Beyond Ultraviolet Radiation—Effective Sun Protection Has to Include Protection Against Infrared a Radiation-Induced Skin Damage," *Skin Pharmacology and Physiology*, 23(1), pp. 15-17 (Jan. 14, 2010).

Tanaka et al., "Near-Infrared Irradiation Non-thermally Affects Subcutaneous Adipocytes and Bones," *Eplasty*, 11(e12), pp. 97-105 (Mar. 9, 2011).

Tanaka et al., "Near-Infrared Irradiation Nontheimally Induces Long-lasting Vasodilation by Causing Apoptosis of Vascular Smooth Muscle Cells," *Eplasty*, 11(e22), pp. 203-211 (May 2, 2011).

Al-Awami et al., "Low Level Laser Therapy for Treatment of Primary and Secondary Raynaud's Phenomenon," *Vasa*, 33(1), pp. 25-29 (Feb. 2004).

Avery et al., "A Controlled Study of Repetitive Transcranial Magnetic Stimulation in Medication-Resistant Major Depression," *Biol Psychiatry*, 59(2), pp. 187-194 (Jan. 15, 2006).

Avni et al., "Protection of Skeletal Muscles from Ischemic Injury: Low-Level Laser Therapy Increases Antioxidant Activity," *Photomed Laser Surg*, 23(3), pp. 273-277 (Jun. 2005).

Baxter et al., "Reduction of Prefrontal Cortex Glucose Metabolism Common to Three Types of Depression," *Arch Gen Psychiatry*, 46(3), pp. 243-250 (Mar. 1989).

Bech et al., "Meta-Analysis of Randomised Controlled Trials of Fluoxetine v. Placebo and Tricyclic Antidepressants in the Short-Term Treatment of Major Depression," *Br J Psychiatry*, 176(5), pp. 421-428 (May 2000).

Bench et al., "The Anatomy of Melancholia—Focal Abnormalities of Cerebral Blood Flow in Major Depression," *Psychol Med*, 22(3), pp. 607-615 (Aug. 1992).

Bogen, "Split-Brain Basics: Relevance for the Concept of One's Other Mind," *J Am Acad Psychoanal*, 28(2), pp. 341-369 (Summer 2000).

Boggio et al., "A Randomized, Double-Blind Clinical Trial on the Efficacy of Cortical Direct Current Stimulation for the Treatment of Major Depression," *Int J Neuropsychopharmacol*, 11(2), pp. 249-254 (Mar. 2008).

Brody et al., "Brain Metabolic Changes in Major Depressive Disorder from Pre- to Post-Treatment with Paroxetine," *Psychiatry Res*, 91(3), pp. 127-139 (Oct. 11, 1999).

Castano et al., "Low-Level Laser Therapy for Zymosan-Induced Arthritis in Rats: Importance of Illumination Time," *Lasers Surg Med*, 39(6), pp. 543-550 (Jul. 2007).

Chen et al., "Role of Reactive Oxygen Species in Low Level Light Therapy," Mechanisms for Low-Light Therapy IV, The International Society for Optical Engineering, doi: 10.1117/1112.814890 (Feb. 18, 2009).

Coffey et al., "Quantitative Cerebral Anatomy of the Aging Human Brain: A Cross-Sectional Study Using Magnetic Resonance Imaging," *Neurology*, 42(3 Pt 1), pp. 527-536 (Mar. 1992).

Cohen et al., "Repetitive Transcranial Magnetic Stimulation of the Right Dorsolateral Prefrontal Cortex in Posttraumatic Stress Disorder: A Double-Blind, Placebo-Controlled Study," *Am J Psychiatry*, 161(3), pp. 515-524 (Mar. 2004).

Conlan et al., "Biostimulation of Wound Healing by Low-Energy Laser Irradiation: A Review," *J Clin Periodontol*, 23(5), pp. 492-496 (May 1996).

DeTaboada et al., "Transcranial Application of Low-Energy Laser Irradiation Improves Neurological Deficits in Rats Following Acute Stroke," *Lasers Surg Med*, 38(1), pp. 70-73 (Jan. 2006).

Doris et al., "Depressive Illness," *Lancet*, 354(9187), pp. 1369-1375 (Oct. 16, 1999).

Drevets et al., "A Functional Anatomical Study of Unipolar Depression," *J Neurosci*, 12(9), pp. 3628-3641 (Sep. 1992).

Drevets et al., "Subgenual Prefrontal Cortex Abnormalities in Mood Disorders," *Nature*, 386(24), pp. 824-827 (Apr. 1997).

Eschweiler et al., "Clinical Efficacy and Cognitive Side Effects of Bifrontal Versus Right Unilateral Electroconvulsive Therapy (ECT): A Short-Term Randomised Controlled Trial in Pharmaco-Resistant Major Depression," *J Affect Disord*, 101(1), pp. 149-157 (Aug. 2007).

Fahim et al., "Abnormal Prefrontal and Anterior Cingulate Activation in Major Depressive Disorder During Episodic Memory Encoding of Sad Stimuli," *Brain and Cognition*, 54(2), pp. 161-163 (Mar. 2004).

Fink, "Convulsive Therapy: A Review of the First 55 Years," *J Affect Disord*, 63(1-3), pp. 115 (Mar. 2001).

Fitzgerald et al., "Transcranial Magnetic Stimulation in the Treatment of Depression: A Double-Blind, Placebo-Controlled Trial," *Arch Gen Psychiatry*, 60(10), pp. 1002-1008 (Oct. 2003).

Gershon et al., "Transcranial Magnetic Stimulation in the Treatment of Depression," *Am J Psychiatry*, 160, pp. 835-845 (May 2003).

Goldman, "Can Aimé Limoge Sell Electroanesthesia to North America?" *Can Med Assoc J*, 130, pp. 1191-1200, (May 1, 1984).

Grunhaus et al., "A Randomized Controlled Comparison of Electroconvulsive Therapy and Repetitive Transcranial Magnetic Stimulation in Severe and Resistant Nonpsychotic Major Depression," *Biol Psychiatry*, 53(4), pp. 324-331 (Feb. 15, 2003).

Hamilton, "A Rating Scale for Depression," *J Neurol Neurosurg Psychiatry*, 23, pp. 56-62 (Feb. 1960).

Hamilton, "The Assessment of Anxiety States by Rating," *Br J Med Psychol*, 32(1), pp. 50-55 (1959).

Hawkins et al., "Low Level Laser Therapy (LLLT) as an Effective Therapeutic Modality for Delayed Wound Healing," *Ann NY Acad Sci*, 1056, pp. 486-493 (Nov. 2005).

Henriques et al., "Left Frontal Hypoactivation in Depression," *J Abnorm Psychol*, 100(4), pp. 535-545 (Nov. 1991).

Hirschl et al., "Low Level Laser Therapy in Primary Raynaud's Phenomenon—Results of a Placebo Controlled, Double Blind Intervention Study," *J Rheumatol*, 31(12), pp. 2408-2412 (Dec. 2004).

Hoge et al., "Combat Duty in Iraq and Afghanistan, Mental Health Problems, and Barriers to Care," *N Engl J Med*, 351(1), pp. 13-22 (Jul. 1, 2004).

Hoge et al., "Mental Health Problems, Use of Mental Health Services, and Attrition from Military Service After Returning from Deployment to Iraq or Afghanistan," *JAMA*, 295(9), pp. 1023-1032 (Mar. 1, 2006).

Huang et al., "Biphasic Dose Response in Low Level Light Therapy," *Dose Response*, 7(4), pp. 358-383 (Sep. 1, 2009).

Hurwitz et al., "Regional Cerebral Glucose Metabolism in Major Depressive Disorder," *Can J Psychiatry*, 35(8), pp. 684-688 (Nov. 1990).

(56) References Cited

OTHER PUBLICATIONS

Ilic et al., "Effects of Power Densities, Continuous and Pulse Frequencies, and Number of Sessions of Low-Level Laser Therapy on Intact Rat Brain," Photomed Laser Surg, 24(4), pp. 458-466 (Aug. 2006).
"INVOS 5100C Cerebral/Somatic Oximeter," INVOS® System Specifications, Somanetics Corporation (Aug. 2008).
Janicak et al., "Repetitive Transcranial Magnetic Stimulation Versus Electroconvulsive Therapy for Major Depression: Preliminary Results of a Randomized Trial," Biol Psychiatry, 52(10), pp. 659-667 (Nov. 15, 2002).
Katz et al., "Onset and Early Behavioral Effects of Pharmacologically Different Antidepressants and Placebo in Depression," Neuropsychopharmacology, 29, pp. 566-579 (Sep. 3, 2003).
Keedwell et al., "The Neural Correlates of Anhedonia in Major Depressive Disorder," Biol Psychiatry, 58(11), pp. 843-853 (Dec. 1, 2005).
Kennedy et al., "Changes in Regional Brain Glucose Metabolism Measured with Positron Emission Tomography after Paroxetine Treatment of Major Depression," Am J Psychiatry, 158(6), pp. 899-905 (Jun. 2001).
Kessler et al., "Sex and Depression in the National Comorbidity Survey I: Lifetime Prevalence, Chronicity and Recurrence," J Affect Disord, 29(2-3), pp. 85-96 (Oct.-Nov. 1993).
Kozel et al., "Meta-Analysis of Left Prefrontal Repetitive Transcranial Magnetic Stimulation (rTMS) to Treat Depression," J Psychiatr Prac, 8(5), pp. 270-275 (Sep. 2002).
Kubota, "Effects of Diode Laser Therapy on Blood Flow in Axial Pattern Flaps in the Rat Model," Lasers Med Sci, 17(3), pp. 146-153 (2002).
Lampl et al., "Infrared Laser Therapy for Ischemic Stroke: A New Treatment Strategy: Results of the NeuroThera Effectiveness and Safety Trial-1 (NEST-1)," Stroke 38, pp. 1843-1849 (Jun. 2007).
Lapchak et al., "Transcranial Near-Infrared Light Therapy Improves Motor Function Following Embolic Strokes in Rabbits: An Extended Therapeutic Window Study Using Continuous and Pulse Frequency Delivery Modes," Neuroscience, 148(4), pp. 907-914 (Sep. 21, 2007).
Leichsenring et al., "Short-Term Psychodynamic Psychotherapy and Cognitive-Behavioral Therapy in Generalized Anxiety Disorder: A Randomized, Controlled Trial," Am J Psychiatry, 166(8), pp. 875-881 (Aug. 2009).
Limoge et al., "Transcutaneous Cranial Electrical Stimulation (TCES): A Review 1998," Neurosci Biobehav Rev., 23(4), pp. 529-538 (Mar. 1999).
Loo et al., "A Review of the Efficacy of Transcranial Magnetic Stimulation (TMS) Treatment for Depression, and Current and Future Strategies to Optimize Efficacy," J Affect Disord, 88(3), pp. 255-267 (Nov. 2005).
Loo et al., "A Sham-Controlled Trial of the Efficacy and Safety of Twice-Daily rTMS in Major Depression," Psychol Med, 37(3), pp. 341-349 (Dec. 19, 2006).
Mayberg et al., "Deep Brain Stimulation for Treatment-Resistant Depression," Neuron, 45(5), pp. 651-660 (Mar. 3, 2005).
Mayberg, "Modulating Dysfunctional Limbic-Cortical Circuits in Depression: Towards Development of Brain-Based Algorithms for Diagnosis and Optimised Treatment," Br Med Bull, 65(1), pp. 193-207 (Mar. 2003).
Mayes et al., "DSM-III and the Revolution in the Classification of Mental Illness," J Hist Behav Sci, 41(3), pp. 249-267 (Summer 2005).
Michalikova et al., "Emotional Responses and Memory Performance of Middle-Aged CD1 Mice in a 3D Maze: Effects of Low Infrared Light," Neurobiol Learn Mem, 89, pp. 480-488 (Sep. 12, 2007).
Mills et al., "Trauma and Stress Response Among Hurricane Katrina Evacuees," Am J Public Health, 97(S1), pp. S116-S123 (Apr. 2007).
Miniussi et al., "Repetitive Transcranial Magnetic Stimulation (rTMS) at High and Low Frequency: An Efficacious Therapy for Major Drug-Resistant Depression?" Clin Neurophysiol, 116(5), pp. 1062-1071 (May 2005).
Mochizuki-Oda et al., "Effects of Near-Infra-Red Laser Irradiation on Adenosine Triphosphate and Adenosine Diphosphate Contents of Rat Brain Tissue," Neurosci Lett, 323(3), pp. 207-210 (May 2002).
Moncrieff et al., "Efficacy of Antidepressants in Adults," British Medical Journal, 331, pp. 155-157 (Jul. 16, 2005).
Montgomery et al., "The Efficacy of Pregabalin and Benzodiazepines in Generalized Anxiety Disorder Presenting with High Levels of Insomnia," Int Clin Psychopharmacol, 24(4), pp. 214-220 (Jul. 2009).
Moshkovska et al., "It Is Time to Test Low Level Laser Therapy in Great Britain," Postgrad Med J, 81(957), pp. 436-441 (Jul. 2005).
Murray et al., "Global Mortality, Disability, and the Contribution of Risk Factors: Global Burden of Disease Study," Lancet, 349(9063), pp. 1436-1442 (May 17, 1997).
Navarro et al., "Normalization of Frontal Cerebral Perfusion in Remitted Elderly Major Depression: A 12-month Follow-Up SPECT Study," NeuroImage, 16(3 pt 1), pp. 781-787 (Jul. 2002).
Nemeroff et al., "Treatment of Mood Disorders," Nature Neuroscience, 5, pp. 1068-1070 (Nov. 2002).
Nitsche et al., "Treatment of Depression with Transcranial Direct Current Stimulation (tDCS): A Review," Exp Neurol, 219(1), pp. 14-19 (Sep. 2009).
Öngür et al., "Glial Reduction in the Subgenual Prefrontal Cortex in Mood Disorders," Proc Natl Acad Sci USA, 95(22), pp. 13290-13295 (Oct. 1998).
Oron et al., "Attenuation of Infarct Size in Rats and Dogs after Myocardial Infarction by Low-Energy Laser Irradiation," Lasers Surg Med, 28(3), pp. 204-211 (Apr. 2, 2001).
Oron et al., "Ga-As (808 nm) Laser Irradiation Enhances ATP Production in Human Neuronal Cells in Culture," Photomed Laser Surg, 25(3), pp. 180-182 (Jul. 2007).
Oron et al., "Low-Level Laser Therapy Applied Transcranially to Rats after Induction of Stroke Significantly Reduces Long-Term Neurological Deficits," Stroke, 37, pp. 2620-2624 (Oct. 2006).
Oron, "Photoengineering of Tissue Repair in Skeletal and Cardiac Muscles," Photomed Laser Surg, 24(2), pp. 111-120 (May 17, 2006).
Pfefferbaum, "Posttraumtic Stress Disorder in Children: A Review of the Past 10 Years," J Am Acad Child Adolesc Psychiatry, 36(11), pp. 1503-1511 (Nov. 1997).
Phillips et al., "Neurobiology of Emotion Perception II: Implications for Major Psychiatric Disorders," Biol Psychiatry, 54(5), pp. 515-528 (Sep. 1, 2003).
Pridmore et al., "Comparison of Unlimited Numbers of Rapid Transcranial Magnetic Stimulation (rTMS) and ECT Treatment Sessions in Major Depressive Episode," Int J Neuropsychopharmacol, 3(2), pp. 129-134 (Jan. 2000).
Rajkowska et al., "GABAergic Neurons Immunoreactive for Calcium Binding Proteins are Reduced in the Prefrontal Cortex in Major Depression," Neuropsychopharmacology, 32(2), pp. 471-482 (Feb. 2007).
Rajkowska et al., "Morphometric Evidence for Neuronal and Glial Prefrontal Cell Pathology in Major Depression," Biol Psychiatry, 45(9), pp. 1085-1098 (May 1, 1999).
Reddy, "Photobiological Basis and Clinical Role of Low-Intensity Lasers in Biology and Medicine," J Clin Laser Med Surg, 22(2), pp. 141-150 (Jul. 8, 2004).
Schaffer et al., "Effects of 780 nm Diode Laser Irradiation on Blood Microcirculation: Preliminary Findings on Time-Dependent T1-Weighted Contrast-Enhanced Magnetic Resonance Imaging (MRI)," J Photochem Photobiol B, 54(1), pp. 55-60, (Jan. 2000).
Schiffer, "Affect Changes Observed with Right Versus Left Lateral Visual Field Stimulation in Psychotherapy Patients: Possible Physiological, Psychological, and Therapeutic Implications," Compr Psychiatry, 38(5), pp. 289-295 (Sep.-Oct. 1997).
Schiffer, "Can the Different Cerebral Hemispheres Have Distinct Personalities? Evidence and its Implications for Theory and Treatment of PTSD and Other Disorders," J Trauma Dissociation, 1(2), pp. 83-104 (Jun. 2000).
Schiffer et al., "Determination of Hemispheric Emotional Valence in Individual Subjects: A New Approach with Research and Therapeutic Implications," Behav Brain Funct, 3(13), pp. 1-21 (Mar. 6, 2007).

(56) References Cited

OTHER PUBLICATIONS

Schiffer et al., "Different Psychological Status in the Two Hemispheres of Two Split-Brain Patients," Neuropsychiatry neuropsychol Behav Neurol, 11(3), pp. 151-156 (Jul. 1998).
Schiffer et al., "Electroencephalogram, Bilateral Ear Temperature, and Affect Changes Induced by Lateral Visual Field Stimulation," Compr Psychiatry, 40(3), pp. 221-225 (May-Jun. 1999).
Schiffer et al., "Lateral Visual Field Stimulation Reveals Extrastriate Cortical Activation in the Contralateral Hemisphere: An fMRI Study," Psychiatry Res, 131(1), pp. 1-9 (May 30, 2004).
Schiffer, "Of Two Minds: The Revolutionary Science of Dual-Brain Psychology," The Free Press, pp. 1-21 (Sep. 28, 1998).
Schiffer et al., "Prediction of Clinical Outcomes from rTMS in Depressed Patients with Lateral Visual Field Stimulation: A Replication," J Neuropsychiatry Clin Neurosci, pp. 194-200 (Spring 2008).
Schiffer et al., "Prediction of Clinical Response to Transcranial Magnetic Stimulation for Depression by Baseline Lateral Visual Stimulation," Neuropsychiatry, Neuropsychology, and Behavioral Neurology, 15, pp. 18-27 (Mar. 2002).
Schiffer et al., "Psychological Benefits 2 and 4 Weeks After a Single Treatment with Near Infrared Light to the Forehead: A Pilot Study of 10 Patients with Major Depression and Anxiety," Behavioral and Brain Functions, 5(46), pp. 1-13 (Dec. 8, 2009).
Schlenger et al., "Psychological Reactions to Terrorist Attacks: Findings from the National Study of Americans' Reactions to Sep. 11," JAMA, 288(5), pp. 581-588 (Aug. 7, 2002).
Shefer et al., "Low-Energy Laser Irradiation Promotes the Survival and Cell Cycle Entry of Skeletal Muscle Satellite Cells," J Cell Sci, 115(7), pp. 1461-1469 (Apr. 1, 2002).
Slade et al., "2007 National Survey of Mental Health and Wellbeing: Methods and Key Findings," Aust N Z J Psychiatry, 43(7), pp. 594-605 (Jan. 2009).
Spitzer et al., "The Structured Clinical Interview for DSM-III-R (SCID). I: History, Rationale, and Description," Arch Gen Psychiatry, 49, pp. 624-629 (Aug. 1992).
Stern et al., "Antidepressant Effects of High and Low Frequency Repetitive Transcranial Magnetic Stimulation to the Dorsolateral Prefrontal Cortex: A Double-Blind, Randomized, Placebo-Controlled Trial," J Neuropsychiatry Clin Neurosci, 19, pp. 179-186 (Spring 2007).
Tadic et al., "Early Improvement is a Predictor of Treatment Outcome in Patients with Mild Major, Minor or Subsyndromal Depression," J Affect Disord, pp. 86-93 (May 9, 2009).
Tew et al., "Relapse During Continuation Pharmacotherapy after Acute Response to ECT: A Comparison of Usual Care versus Protocolized Treatment," Aim Clin Psychiatry, 19(1), pp. 1-4 (Jan.-Mar. 2007).
Tuby et al., "Modulations of VEGF and iNOS in the Rat Heart by Low Level Laser Therapy are Associated with Cardioprotection and Enhanced Angiogenesis," Lasers Surg Med, 38(7), pp. 682-688 (Aug. 2006).
Vasterling et al., "Neuropsychological Outcomes of Army Personnel Following Deployment to the Iraq War," JAMA, 296(5), pp. 519-529 (Aug. 2, 2006).
Watson et al., "Development and Validation of Brief Measures of Positive and Negative Affect: The PANAS Scales," J Pers Soc Psychol, 54(6), pp. 1063-1070 (Jun. 1988).
Woodruff et al., "The Efficacy of Laser Therapy in Wound Repair: A Meta-Analysis of the Literature," Photomed Laser Surg, 22(3), pp. 241-247 (Jun. 2004).
Yaakobi et al., "Long-Term Effect of Low Energy Laser Irradiation on Infarction and Reperfusion Injury in the Rat Heart," J Appl Physiol, 90(6), pp. 2411-2419 (Jun. 2001).
Yu et al., "Photomodulation of Oxidative Metabolism and Electron Chain Enzymes in Rat Liver Mitochondria," Photochem Photobiol, 66(6), pp. 866-871 (Dec. 1997).
Zhang et al., "cDNA Microarray Analysis of Gene Expression Profiles in Human Fibroblast Cells Irradiated with Red Light," J Invest Dermatol, 120(5), pp. 849-857 (May 2003).
Zivin et al., "Effectiveness and Safety of Transcranial Laser Therapy for Acute Ischemic Stroke," Stroke, 40, pp. 1359-1364 (Apr. 2009).
PCT International Search Report Based on PCT/US2010/045327 dated Oct. 4, 2010.

METHODS FOR TREATING PSYCHIATRIC DISORDERS USING LIGHT ENERGY

RELATED APPLICATIONS

This application is a continuation of copending U.S. Utility application Ser. No. 13/481,820, filed on May 26, 2012, which claims the benefit of U.S. Utility application Ser. No. 12/855,258, filed on Aug. 12, 2010, which claims the benefit of priority from U.S. Provisional Patent Application No. 61/233,318, filed on Aug. 12, 2009, the entireties of each which are hereby incorporated herein by reference.

FIELD

The embodiments disclosed herein relate to the treatment of psychiatric disorders, and more particularly to the treatment of psychiatric disorders using light energy.

BACKGROUND

The application of intense light, a non-ionizing phototherapy, has been reported in over a thousand scientific publications to have therapeutic efficacy for a wide range of disorders in humans without any observed harmful effects. Light has been demonstrated in cell culture to increase mitochondrial respiration, increase ATP synthesis, increase heat shock proteins, induce transforming growth factor β-1, and increase nerve cell proliferation and migration. Light has been tested in animals to facilitating wound healing, promote the process of skeletal muscle regeneration, and reduce infarct size in ischemic heart muscle by 50 to 70% in an induced experimental model in rats and dogs. Light in the near infrared spectrum, which penetrates the scalp and skull, can significantly reduce damage from experimentally induced stroke in rats and rabbits, and to improve the memory performance of middle aged mice, and reduce damage from acute stroke in humans. A method of treating psychiatric disorders using light energy is needed.

SUMMARY

Methods for treating psychiatric disorders using light energy are disclosed herein.

According to aspects illustrated herein, there is provided a method for treating psychiatric disorders using light energy, including determining which hemisphere of the brain requires treatment using lateral visual field stimulation (LVFS) and applying light energy to the hemisphere of the brain to treat the psychiatric disorder other than depression. In an embodiment, light energy may include near infrared light (NIR). The methods of the present disclosure may be used to treat a variety of psychiatric disorders.

According to aspects illustrated herein, there is provided a method for treating a psychiatric disorder in a patient, including measuring a left hemispheric emotional valence and a right hemispheric emotional valence for a left hemisphere of the brain and a right hemisphere of the brain using a lateral visual field stimulation test; determining which hemisphere of the brain needs treatment; and applying light energy to the hemisphere of the brain to treat the psychiatric disorder co-morbid with depression.

According to aspects illustrated herein, there is provided a method for treating a psychiatric disorder in a patient, including measuring a left hemispheric emotional valence for a left hemisphere of the brain and a right hemispheric emotional valence for a right hemisphere of the brain using a lateral visual field stimulation test; determining the hemisphere of the brain in need of treatment; and applying light energy to the hemisphere of the brain to treat the psychiatric disorder co-morbid with depression.

According to aspects illustrated herein, there is provided a method for treating psychiatric disorders using light energy, including determining which hemisphere of the brain has a more positive psychology or valence, using lateral visual field stimulation (LVFS), and applying light energy to the hemisphere with the more positive valence. In an embodiment, light energy may include near infrared light (NIR). The methods of the present disclosure may be used to treat a variety of psychiatric disorders.

According to aspects illustrated herein, there is provided a method for treating psychiatric disorders using light energy, including determining which hemisphere of the brain has a more negative psychology or valence, using lateral visual field stimulation (LVFS), and applying light energy to the hemisphere with the more negative valence to improve its functioning. In an embodiment, light energy may include near infrared light (NIR). The methods of the present disclosure may be used to treat a variety of psychiatric disorders.

According to aspects illustrated herein, there is provided a method for treating psychiatric disorders using light energy, including determining which hemisphere of the brain has a more positive and negative psychology or valence, using lateral visual field stimulation (LVFS); applying light energy to the hemisphere with the more positive affect; and applying light energy to the hemisphere with the more negative effect. In an embodiment, if both hemispheres have about equal levels of positive or negative valence, both hemispheres may benefit from the light energy. In an embodiment, light energy may include near infrared light (NIR). The methods of the present disclosure may be used to treat a variety of psychiatric disorders.

According to aspects illustrated herein, there is provided a method for treating psychiatric disorders using light energy, including determining which hemisphere of the brain has a more negative psychology or valence, using lateral visual field stimulation (LVFS); applying light energy to the hemisphere with the more negative affect; and increasing cerebral blood flow in the opposing hemisphere. In an embodiment, light energy may include near infrared light (NIR). The methods of the present disclosure may be used to treat a variety of psychiatric disorders.

According to aspects illustrated herein, there is provided method for treating a patient, including determining which portion of the brain of the patient requires treatment; and applying light energy to the portion to treat the patient. The light might be applied bilaterally over the left and the right dorsolateral pre-frontal coracles. In an embodiment, the treatment may be used to treat depression. In another embodiment, the treatment may be used to improve the well-being of the patient.

According to aspects illustrated herein, there is provided a method for treating a patient, including determining which portion of the brain needs treatment; and applying light energy to the portion of the brain to treat the patient. In an embodiment, the treatment may be used to treat depression. In an embodiment, the treatment may be used to cause an improvement in the well-being of the patient.

According to aspects illustrated herein, there is provided a method for treating a psychiatric disorder in a patient including applying light energy to a brain to treat the psychiatric disorder.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 2A shows brain activity after looking out of the left half of the left eye (the left lateral visual field). FIG. 2B shows brain activity after looking out of the right half of the right eye (the right lateral visual field).

Figure 1:
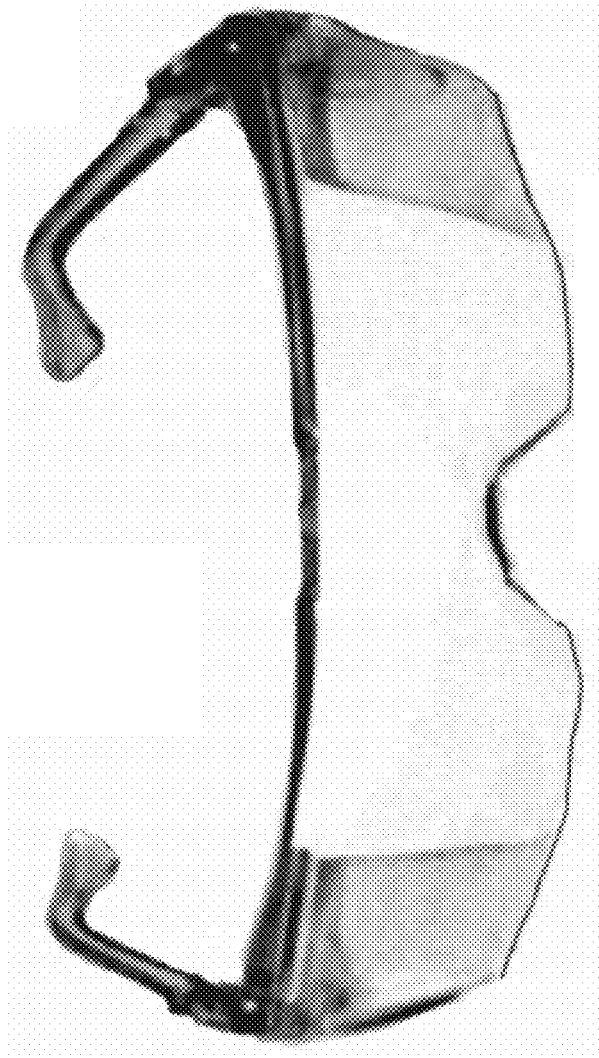
FIG. 1 shows a front view of glasses used for lateral visual field stimulation.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Methods of treating psychiatric or psychological disorders using light energy are disclosed herein. The methods of the present disclosure may include using lateral visual field stimulation (LVFS) to determine which hemisphere of the brain requires treatment. Light energy may be applied to the chosen hemisphere to treat the psychological disorder. In an embodiment, the light energy may include near infrared light (NIR). The methods of the present disclosure may be used to treat a variety of psychological disorders.

As used herein, the terms "depression," "depressive disorder," "dysthymic disorder," "major depressive disorder" and "unipolar depression" refer to a DSM-IV definition of depression.

As used herein, the term "psychiatric disorders" refers to any psychiatric disorders including, but not limited to, depression, attention deficit disorder, schizophrenia, bipolar disorder, anxiety disorders, alcoholism, eating disorders such as anorexia and bulimia, phobias, Asperser's syndrome, dissociative disorders, insomnia, and borderline personality disorder. The DSM-IV definition applies to these psychiatric disorders. Psychiatric disorders also include substance abuse disorders (i.e., alcohol abuse or opiate dependence or abuse) caused either by depression or not caused by depression, persistent anxiety, anxiety attacks, feelings of panic, fears of social contacts, nightmares, flashbacks, obsessive thoughts, compulsive behavior, attention disorder, sexual problem, and irrational thinking.

As used herein, the term "co-morbid" or "co-existent" refers to any psychiatric disorders that exist in addition to a primary disease or disorder, such as depression.

As used herein, the term "transcranial" refers to a procedure that is performed through the cranium, or the skull that covers and protects the brain. Transcranial refers to a noninvasive method that delivers energy to the neurons of the brain. Transcranial therapy can cause activity in specific or general parts of the brain with minimal discomfort, allowing the functioning and interconnections of the brain to be studied and/or treated. The light device is held on the scalp, no actual contact is necessary, and the energy passes through the skull and into the brain. Small induced currents can then make brain areas below the light device more or less active, depending on the settings used.

As used herein, the term "treat", "treating" or "stimulating" refers to enhancing a person's positive outlook or suppressing a person's negative outlook. This may refer to a person's psychological well-being, including but not limited to their emotional, cognitive, and motivational states. Those persons who are successfully treated can find more appreciation for life, for themselves (improved self-esteem), their work, and their personal relationships.

Well-being refers to a state of wellness of body, mind and soul, where all are in a state of health, the individual is happy and prospering. Well-being describes the overall welfare of an individual including a good or satisfactory condition of existence. Well-being is a state characterized by health, happiness, and prosperity.

Psychiatric disorders include, but are not limited to, depression, attention deficit disorder, schizophrenia, bipolar disorder, anxiety disorders, alcoholism, eating disorders such as anorexia and bulimia, phobias, Asperser's syndrome, dissociative disorders, insomnia and borderline personality disorder. One prevalent psychiatric disorder is depression. Depression may be defined as a combination of sadness, loss of energy, feelings of hopelessness, difficulty concentrating, insomnia, and irritability. The National Comorbidity Survey reported that 46% of men and 58% of women have suffered in their lifetime at least a two-week period in which they experienced a persistent depressed mood. Major depression has a lifetime prevalence of about 16%, and it is estimated that by 2020, it will be the second greatest contributor to the impairment of global health. A recent Australian survey reported that anxiety disorders were the most common mental disorder with a lifetime prevalence of 26%.

In psychiatry, the Diagnostic and Statistical Manual of Mental Disorders, 4th Edition (DSM-IV) is a manual published by the American Psychiatric Association (APA) that includes all currently recognized mental health disorders. In the DSM-IV, there are two diagnoses for depression, Major Depression and Dysthymic Disorder, as described below.

Major Depressive Disorder is characterized by one or more Major Depressive Episodes (i.e., at least 2 weeks of depressed mood or loss of interest accompanied by at least four additional symptoms of depression). Dysthymic Disorder is characterized by at least 2 years of depressed mood for more days than not, accompanied by additional depressive symptoms that do not meet criteria for a Major Depressive Episode.

Criteria for Major Depressive Episode Include:

A. Five (or more) of the following symptoms have been present during the same 2-week period and represent a change from previous functioning; at least one of the symptoms is either (1) depressed mood or (2) loss of interest or pleasure. Note: Do not include symptoms that are clearly due to a general medical condition, or mood-incongruent delusions or hallucinations.

(1) depressed mood most of the day, nearly every day, as indicated by either subjective report (e.g., feels sad or empty) or observation made by others (e.g., appears tearful). Note: In children and adolescents, can be irritable mood.

(2) markedly diminished interest or pleasure in all, or almost all, activities most of the day, nearly every day (as indicated by either subjective account or observation made by others)

(3) significant weight loss when not dieting or weight gain (e.g., a change of more than 5% of body weight in a month), or decrease or increase in appetite nearly every day. Note: In children, consider failure to make expected weight gains.

(4) insomnia or hypersomnia nearly every day (5) psychomotor agitation or retardation nearly every day (observable by others, not merely subjective feelings of restlessness or being slowed down)

(6) fatigue or loss of energy nearly every day (7) feelings of worthlessness or excessive or inappropriate guilt (which may be delusional) nearly every day (not merely self-reproach or guilt about being sick)

(8) diminished ability to think or concentrate, or indecisiveness, nearly every day (either by subjective account or as observed by others)

(9) recurrent thoughts of death (not just fear of dying), recurrent suicidal ideation without a specific plan, or a suicide attempt or a specific plan for committing suicide B. The symptoms do not meet criteria for a Mixed Episode.

C. The symptoms cause clinically significant distress or impairment in social, occupational, or other important areas of functioning.

D. The symptoms are not due to the direct physiological effects of a substance (e.g., a drug of abuse, a medication) or a general medical condition (e.g., hypothyroidism).

E. The symptoms are not better accounted for by Bereavement, i.e., after the loss of a loved one, the symptoms persist for longer than 2 months or are characterized by marked functional impairment, morbid preoccupation with worthlessness, suicidal ideation, psychotic symptoms, or psychomotor retardation.

Diagnostic Criteria for Dysthymic Disorder Include:

A. Depressed mood for most of the day, for more days than not, as indicated either by subjective account or observation by others, for at least 2 years. Note: In children and adolescents, mood can be irritable and duration must be at least 1 year.

B. Presence, while depressed, of two (or more) of the following:

(1) poor appetite or overeating
(2) insomnia or hypersomnia
(3) low energy or fatigue
(4) low self-esteem
(5) poor concentration or difficulty making decisions
(6) feelings of hopelessness The DSM-IV (1), the International Classification of Diseases (ICD-9-CM)(2), and as described in The Comprehensive Textbook of Psychiatry (3), thus, define depressive disorders, which in the DSM-IV and the ICD-9-CM are given specific diagnostic codes: major depression is 962.3 and dysthymia is 300.4. In distinction from the depressive disorders, the DSM-IV, ICD-9-CM, the Comprehensive Textbook of Psychiatry, and the accepted practice in the profession (4) consider other disorders as separated and distinct psychiatric diagnoses. The DSM-IV list of major categories is as follows:

Disorders Usually First Diagnosed in Infancy, Childhood, or Adolescence

Delirium, Dementia, and Amnestic and Other Cognitive Disorders

Mental Disorders Due to a General Medical Condition

Substance-Related Disorders

Schizophrenia and Other Psychotic Disorders

Mood Disorders

Anxiety Disorders

Somatoform Disorders

Factitious Disorders

Dissociative Disorders

Sexual and Gender Identity Disorders

Eating Disorders

Sleep Disorders

Impulse-Control Disorders Not Elsewhere Classified

Adjustment Disorders

Personality Disorders

Other Conditions That May Be a Focus of Clinical Attention

The depressive disorders are listed under Mood Disorders. The profession considers other diagnostic categories distinct and separate from depressive disorders in terms of diagnosis, treatment, clinical course, symptoms, genetics, and brain pathophysiology. For example, electro-convulsive therapy is commonly used to treat major depression, but is not used for childhood disorders, dementia, mental disorders due to a general medical condition, substance-related disorders, anxiety disorders, somatoform disorders, factitious disorders, dissociative disorders, sexual and gender identity disorders, eating disorders, sleep disorders, impulse-control disorders, adjustment disorders or personality disorders. Benzodiazepams such as diazepam or klonazepam are common treatments for anxiety disorders but are likely to make depressed patients more depressed. Schizophrenia is treated with antipsychotic medications that, with a few exceptions, are only used to treat psychotic patients. Buprenorphine is used to treat opiate dependence, but is not approved for any other diagnosis. Disulfiram is used only in the treatment of alcohol dependence.

Depression can run in families, and usually starts between the ages of 15 and 30. It is much more common in women. Women can also get postpartum depression after the birth of a baby. Some people get seasonal affective disorder in the winter. Depression is one part of bipolar disorder. There are effective treatments for depression, including antidepressants and talk therapy. Many depressed people do best by using both.

Depression is considered separate and distinct from other psychiatric or psychological disorders. Depression by any definition does not encompass most psychological disorders. For example, people who are diagnosed with schizophrenia have delusions and/or hallucinations, and have a deterioration of their personality rendering them almost always incapable of complex work or sustained relationships. A person with an anxiety disorder will suffer excessive apprehension and worry with heightened arousal, but will not feel sad or hopeless unless he suffers, in addition, a coexisting depressive disorder. A person who abuses substances will usually not also suffer anxiety or depression, although he may have a dual diagnosis in which both a substance abuse disorder and another disorder such as an anxiety disorder or a depressive disorder are also present. 47% of patients diagnosed with schizophrenia also have a substance abuse disorder.

Each of the diagnostic entities in the DSM-IV are supported not only by clinical descriptions, but also by biological studies that use electroencephalography (EEG), magnetoencephalograpy (MEG), functional magnetic resonance imaging (fMRI), evoked potentials, electrodermal activity, biochemical markers (catecholamines and catecholamine metabolites; indoleamines and indoleamine metabolites, acetylcholine, histamine, aminoacids, melatonin, prostaglaindins, opoid petptides, neuropeptides, enzymes, receptor densities), psychoimmunological markers, genetic markers, and animal models.

By modern scientific techniques, depressive disorders and other DSM-IV disorders can be distinguished from each other. For example, as reviewed in the textbook, Current Diagnosis and Treatment: Psychiatry by Loosen and Shelon, antidepressant treatments (including pharmacotherapy and electroconvulsive therapy [ECT]) cause desensitization of the norepinephrine receptor—coupled adenylate cyclase system in brain, which is linked to a decrease in the density of adrenoceptors in the brain. This decrease in receptor sites paralleled the delayed onset of action common to all antidepressants. Further, depression is associated with the integration of multiple intracellular signals that regulate neuronal response (i.e., changes in G protein, cyclic adenosine monophosphate, or protein kinase and the induction of gene transcription). These intracellular signals ultimately affect the expression of specific genes. It is these abnormalities of intracellular signal transduction and/or gene expression that underlie much of the physiology of depression. Other neurotransmitters (e.g., acetylcholine, gamma amino butyric acid, melatonin, glycine, histamine), hormones (e.g., thyroid and adrenal hormones), and neuropeptides (e.g., corticotropin-releasing hormone, endorphins, enkephalins, vasopressin, cholecystokinin, substance P) also play significant roles in the physiology of depression.

In depression, functional imaging studies most consistently demonstrate a decreased prefrontal cortex (PFC), especially left PFC, blood flow. These findings correlate with severity of illness and cognitive impairment. Functional imaging in depressed patients also show basal ganglia abnormalities, involving decreased blood flow and metabolism as well as increased activity of amygdala. In major depression, other neuroimaging studies show abnormalities in the hippocampus, cingulate, and related parts of the striatum and thalamus. Together data offer a neural model for depression in which dysfunction of limbic, striatal, and PFC structures impair the modulation of the amygdala/hippocampus complex and lead to abnormal processing of emotional stimuli. Depression also tends to be associated with lesions in the left frontotemporal or right parieto-occipital regions.

Many patients with dysthymic disorder have brain wave (EEG) abnormalities that mimic those found in major depression such as reduced REM latency, increased REM density, reduced slow-wave sleep, impaired sleep continuity. Patients with dysthymia who have these EEG abnormalities more frequently have a positive family history for major depression. They also respond better to antidepressant medications.

Anxiety disorders have scientific findings that differentiate them from depression and other psychiatric or psychological disorders. In patients with anxiety disorders functional neuroimaging shows abnormalities during symptom provocation tests, in the limbic, paralimbic and sensory association regions.

For anxiety there is a general theory of a neural behavioral-inhibition system. This system evaluates stimuli to attempt to determine their level of dangerousness and simultaneously in response produce behavioral inhibition and increase arousal and attention. Antianxiety drugs inhibit brain areas involved in these responses. From animal studies using pharmacological agents and/or brain lesions, anxiety is associated with several interconnected anatomical areas. Sensory stimuli that are interpreted as dangerous activate the hippocampus, especially the entorhinal cortex, which secondarily induces habituation by actions on the lateral and medial septal areas, which then stimulate the cingulate which induces behavioral inhibition. Several specific neurotransmitter systems influence this anxiety mechanism, including noradrenergic activity of the locus coeruleus, serotonergic systems originating in the raphe, and by widespread GABAA-receptor activity (which are the main locus of activity of the benzodiazepines).

Stimuli that are interpreted as acute threats activate the "fight or flight" response, which is mediated especially by the locus coeruleus and the amygdala. The amygdala encodes fearful memories and aversive conditioning and participates in the acute fear and negative anticipation that we call anxiety.

Further, intense anxiety stimulates the sympathetic nervous system via the locus coeruleus, and this induces tachycardia, tremor, and diaphoresis. The frontal cortex becomes aware of the anxiety and induces behavioral responses which are attempts to improve survival, but which often cause more harm and increase danger. The cingulate, in anxiety disorders, attempts to improve the communication between the cortex and the subcortical areas. Patients with a panic disorder can have a panic attack induced by intravenous sodium lactate or inhalation of 5-35% $CO_2$. This will not affect individuals who do not suffer a panic disorder. These agents activate the locus coeruleus. There is new evidence that 5-HT1A-receptor binding is reduced in some patients with panic disorder.

In an embodiment, the methods of the present disclosure can be used to diagnose and treat the human brain for psychological, psychiatric, depressive, neurological, general well-being and other conditions. In an embodiment, the methods of the present disclosure may include the use of a light treatment device to diagnose and treat depression. In an embodiment, the methods of the present disclosure may be used to diagnose and treat psychiatric disorders other than depression including, but not limited to, attention deficit disorder, schizophrenia, bipolar disorder, anxiety disorders, substance abuse disorders such as alcohol abuse and drug abuse, eating disorders such as anorexia and bulimia, phobias, Asperser's syndrome, dissociative disorders, insomnia, borderline personality disorder or combinations thereof. In an embodiment, the methods of the present disclosure may be used to diagnose and treat other psychiatric or psychological disorders including, but not limited to, persistent anxiety, anxiety attacks, feelings of panic, fears of social contacts, nightmares, flashbacks, alcohol or drug abuse, obsessive thoughts, compulsive behavior, attention disorder, sexual problem, eating disorder such as anorexia, bulimia or obesity, irrational thinking, or combinations thereof. In an embodiment, the methods of the present disclosure may be used to diagnose and treat psychiatric disorders that are co-morbid or co-existent with depression. In an embodiment, the methods of the present disclosure may be used to diagnose and treat more than one psychiatric disorder at a given time. For instance, the method may diagnose and treat a patient having both depression and attention deficit disorder or a patient having both anorexia and insomnia. In an embodiment, the methods of the present disclosure may be used to benefit persons who do not have any psychological disorders. For patients without any of the above psychological disorders, the methods of the present disclosure may help improve their psychological well-being and enhance their positive outlook. These patients can find more appreciation for life, for themselves (improved self-esteem), their work, and their personal relationships. The methods of the present disclosure may improve patient self-confidence, positive disposition, interpersonal relationships, and/or quality of life.

A recently published study was conducted of an open clinical trial of the use of transcranial near infra-red light to treat 10 psychiatric patients (5 males) with a current major depressive disorder with a comorbid anxiety disorder, including 3 with a history of Post-Traumatic Stress Disorder. Schiffer F, Johnston A L, Ravichandran C, Polcari A, Teicher M H, Webb R H, Hamblin M R. Psychological benefits 2 and 4 weeks after a single treatment with near infrared light to the forehead: a pilot study of 10 patients with major depression and anxiety. *Behavioral and Brain Functions*. 2009 Dec. 8; 5:46.

Seven of these patients had a past history of opiate dependence (6 patients) and one had a history of alcohol dependence. The patients were allowed to continue their usual psychiatric treatments, but were asked, if possible to not alter their on-going treatments. None altered their treatments from 2 weeks before the NIR-PBM or during the 4-week follow-up.

As a baseline measure each patient had a Standardized Clinical Diagnostic Interview to determine their diagnosis. The patients also had their hemispheric emotional valence measured using lateral visual field stimulation (LVFS), which includes having a patient look out of one side of taped safety goggles to allow their vision to be restricted on either the left or the right lateral visual field. Earlier studies found that LVFS can induce EEG, ear temperature, and fMRI changes. These results indicate that looking out the right visual field activates the left hemisphere of the brain and that looking out of the left visual field activates the right hemisphere of the brain.

Earlier studies further reported that looking out of one lateral visual field for a minute or more can induce a personality alteration such that one side (left or right) in 80% of patients will induce a more mature personality while looking out of the other visual field will stimulate a personality that is more immature and more negatively effected by past traumas. By measuring the affective state of the patient while he or she looks out of both visual fields we can calculate a hemispheric emotional valence which indicates the degree to which either the left or the right cerebral hemisphere is mature and healthy or immature and neurotic. Some studies suggest that using the patient's hemispheric valence might guide the application of lateralized treatments to the brain for psychiatric conditions as well as help in the evaluation of data from experiments treating one cerebral hemisphere. For example, two similar but different studies reported that the baseline hemispheric emotional valence predicted which patients would respond to left-sided transcranial magnetic stimulation, an FDA approved treatment for depression that applies a powerful electromagnet to the left-side of the head. Both studies suggested that treating a patient who has a positive hemispheric valence in his left hemisphere (the treated hemisphere) will do well, but that patients who have a negative hemispheric emotional valence in their left hemisphere (the treated hemisphere) will not do well.

As another baseline measure each patient was given a Hamilton Depression Rating Scale, a Hamilton Anxiety Rating Scale, and a Positive and Negative Affect Scale. The two Hamilton scales are used to measure changes in depression and in anxiety from a treatment over at least a week. The Positive and Negative Affect Scale is used to measure immediate changes in mood following a treatment.

Each patient's cerebral blood flow in the frontal poles of their brain on both the left and right sides was measured using, for instance, a commercial device. The patients then received 4 treatments. Two treatments were placebo treatments, with the near infrared light turned off, one treatment was over the left side of the forehead and another treatment was over the right-side. The two active treatments consisted of a 4-minute treatment with near infrared light at 240 mW, one on the left-side of the forehead and the other on the right-side. Patients were unable to detect whether the light was on or off, and so the light off condition acted as a placebo condition.

Immediately after each treatment (left-side "on", left-side "off", right-side "on", right-side "off" we measured the patient's affective state with the Positive and Negative Affective Scale. During each treatment we measured the cerebral blood flow in the left and in the right frontal pole of the patient's brain. At two weeks post treatment and at four weeks post-treatment we repeated both of the Hamilton scales.

The study revealed several findings. First, following each of the 4 treatment conditions, the Positive and Negative Affective Scale scores showed an improvement if the side with a positive hemispheric emotional valence was treated but a worsening in the measured affective state if the hemisphere with a negative hemispheric emotional valence were treated. Second, the study found when the left side of the forehead was treated with the light on, the frontal pole blood flow was 0.65±sd 0.08, compared to 0.06±sd 0.05 when the left-side was treated with the light off, placebo condition.

The study also revealed that at 2-weeks post treatment (all 4 treatment conditions were given on the same day) there was a dramatic improvement in both the Hamilton Depression Rating Scale and in the Hamilton Anxiety Rating Scale. Sixty percent of the 10 patients went into a remission defined as a Hamilton Depression Rating Scale score of <10 at 2-weeks post treatment. For the Hamilton Anxiety Rating Scale, 70% achieved a remission at this criteria. These results compare favorably other treatments for depression or anxiety disorders such as cognitive behavior therapy of 30 weeks, serotonin reuptake inhibitors for 8 weeks, a course of transcranial magnetic stimulation or a course of electro-convulsive shock therapy as discussed in our publication. Since the sample of patients included those suffering from major depression, a generalized anxiety disorder, post-traumatic stress disorder, and recent substance abuse, this NIR-PBM treatment might be suitable for additional diagnostic groups.

The study further showed that the outcomes on the Hamilton Anxiety Rating Scale were predicted by an interaction between the individual patient's hemispheric emotional valence times the increase in blood flow in the frontal pole on the side of the positive hemispheric valence. (See FIG. 8)

As a result, the study found that bilateral NIR-PBM treatments led to highly significant improvements 2 weeks post treatment. The study also found that immediately after treatment, patients did well when the hemisphere with a positive valence was treated and poorly when the hemisphere with a negative valence was treated. From this observation, it is likely that treating only the side with a positive hemispheric valence might give better results than the bilateral treatment results at 2-weeks post treatment. The location of treatment is likely also important. Treating over the upper side of the forehead, in an embodiment, is likely to activate the hemisphere while treating over the area of the forehead over the eye may have an inhibitory effect.

The study results are not likely due to placebo effects for several reasons. First, placebo effects are usually on the order of a 20% improvement and our improvement was on the order of 50 to 60%. Second, cerebral blood flow increased when the NIR-PBM was "on" versus the placebo "off" condition. Patients could not determine whether or not the light was on or off. Third, immediately following the treatments, the patients improved to a greater extent when the hemisphere with a positive hemispheric emotional valence was treated. And finally, the Hamilton Anxiety Rating Scale scores were predicted by the product of the lateralized cerebral blood flow and the hemispheric emotional valence.

The methods of the present disclosure can be used with light treatment devices known in the art that deliver light energy for diagnosis and treatment of the human brain for psychological, psychiatric, depressive, neurological, general well-being and other conditions. In one embodiment, the methods of the present disclosure may include the use of lateral visual field stimulation (LVFS) in conjunction with light treatments to help treat a variety of psychiatric disorders or psychological conditions. The brain is at its core an information processor. It takes sensory inputs, interprets them, and decides on a response. A computer is also an information processor that takes inputs and creates responses or outputs. The computer uses transistor states to code information; the brain uses neural firing patterns or biological neural networks to code its information. Like a computer the brain uses parallel and serial processing, and different biological neural networks in the brain operated somewhat independently, but, like a computer in a network, are related to other biological neural networks. The brain's neural networks have hierarchical arrangements. For example, sensory association areas of the brain have biological neural networks that process information from several primary sensory areas (perhaps for hearing, sight, and touch). The biological neural networks in the sensory association areas will relate to higher order association areas in the frontal cortices whose biological neural networks integrate the sensory information with information from other biological neural networks having to do with other functions such as emotion or memory. Each neural network processes information, and as such is a mini-brain, which combines with other biological neural networks to create higher levels of function and eventually create a mind with perceptions, emotions, motivations, and actions or behaviors. A person can have a dominant high-level set of biological neural networks that support his dominant personality, but he may have competing high-level sets of neural networks that support a personality with somewhat different perceptions, emotions, motivations, actions or behaviors. These high level biological neural networks appear to have a relationship with one or the other of the two cerebral hemispheres of the brain. The neural networks associated with one hemisphere (either the left or the right) might be more affected by past traumas and have a more neurotic perception of the world. For example, someone who was bullied as a child, might as an adult, have high level neural networks that incorrectly perceive the world as hostile and threatening. That person may have another set of high level neural networks, associated with the other cerebral hemisphere, that are healthier and see the world (as it now actually is) as safe. Depending on which set of high-level neural networks is dominant at a particular time, the person will manifest a personality that is either troubled or is healthier (or some combination of the two).

Childhood traumas are almost always associated with biological neural networks that are associated with one hemisphere more than the other. Troubled biological neural networks may not be associated with only one hemisphere, but rather they may be associated more with one hemisphere over the other and once stimulated can take over the entire brain. Different set of neural networks can compete for dominance and when in control can use more and more of the brains neurons. In a computer, one program such as Word uses the same transistors that a different program such as Excel uses. The allocation of neurons within the brain may be determined by the struggles between competing sets of biological neural networks.

Each diagnostic entity is manifested by different configurations of biological neural networks involving different brain locations and different neural transmitters and so are distinct entities as described above. However, each entity may involve a healthier and a more pathological set of neural networks that are associated each with one of the two cerebral hemispheres. Which hemisphere is associated with the more pathological neural networks has to be determined for each individual patient. This may refer to a hemispheric valence. The hemisphere with the healthier neural networks is said to have a more positive hemispheric emotional valence. The other cerebral hemisphere is thought to have a more negative hemispheric emotional valence.

This explanation is based mainly on two observations. The first is that we know that the eyes in all people are connected to the brain so that images projected to the left visual field are sent first to the right cerebral hemisphere. The information can then be sent via the corpus callosum to the opposite hemisphere, but in patients in whom the corpus callosum has been severed as a treatment for epilepsy, the image is seen only by one hemisphere. This discovery led to the "Split-brain Studies" for which Roger Sperry won the Nobel Prize. We found that having patients limit their vision to either the left or right lateral visual field while in an fMRI scanner led to the observation illustrated in FIG. 2 that when the patients looked out of their right lateral visual field the blood flow (and presumably their brain activity) in their left brain was dramatically increased. The opposite occurred when the subjects looked out of the left lateral visual field.

In an embodiment, based on earlier publications, having a person look out of one lateral visual field and then the other could cause dramatic changes in the patients' psychological state. About 60% of patients may feel differently when they look out of one visual field versus the other and about 30% have extreme responses. About 85% of patients with severe symptoms will have an extreme response. An example of an extreme response is the following: a patient who is a veteran of the war in Vietnam looked out of his right lateral visual field and saw a large plant behind me and became alarmed. He said, "That plant looks like the jungle!" I asked him quickly to look out of the left lateral visual field and he said, "That's a nice looking plant." He was obviously distressed when looking out the right lateral visual field and was relaxed and calmed when looking out of the left lateral visual field. The side in which the patient gets upset is consistent for that patient, but for another given patient the side that is upsetting can be either the left or right side. Patients with post-traumatic stress disorder, about 65% of the time, feel more distressed when they look out of the right visual field (left brain is more distressed). Patients with major depression about 65% of the time feel more distressed when looking out of the left lateral visual field.

LVFS can be used to guide the placement of light treatments. In an embodiment, LVFS may be used to activate positive neural networks and negative neural networks. The positive neural networks and the negative neural networks in the brain may be associated with positive or negative outlooks on the world, respectively. In an embodiment, traumatic experiences may be associated with specific neural networks that are in some way associated with one hemisphere. Treatment of psychological conditions may include treating these negative neural networks, either through education, suppression, by enhancing the positive neural networks associated with the hemisphere with a positive HEV, psychotherapy, deep brain stimulation, certain psychotropic medications, unilateral ECT, transcranial magnetic stimulation (TMS) or by a combination of methods. In an embodiment, near infrared (NIR) treatments may be used to enhance the positive hemisphere, suppress the negative, and to support the teaching or healing of the negative neural networks so that the trauma can be tolerated, grieved and recovered from. In another embodiment, NIR treatments can be combined with other treatments.

In an embodiment, the methods of the present disclosure may include the use of glasses for the LVFS treatment. As shown in FIG. 1, glasses, such as safety glasses or goggles, are taped or covered so that they permit vision to only one lateral visual field at a time. The patient is asked to look to one side and to fixate the center of his vision on the edge of the tape so that he or she is looking out of the lateral half of one eye. Vision from the other eye is occluded by the tape on the other side. While looking out of the specific visual field, the patient is asked to look at a photograph of a man or woman with a mildly angry facial expression. After 45 seconds, he or she is asked to verbally rate his or her present feelings for each of 10 affects from Positive and Negative Affect Scale (PANAS), from none to extreme on a 5 point scale. Following the PANAS measurements, the patient is asked to rest for 1 minute looking straight ahead so that vision from both eyes is occluded. The patient is then asked to repeat the procedure by looking out of the second visual field.

The PANAS has 5 positive affects including alert, inspired, determined, attentive, active and 5 negative affects including upset, hostile, ashamed, nervous, afraid. For each visual field, the sum of the scores on the 5 negative affects is subtracted from the scores from the 5 positive affects and the difference is the PANAS score. The score measured when the person looks out of the right lateral visual field (RVF) is subtracted from the score measured when the person looks out of the left lateral visual field (LFV). The LVF is indicative of the state of the right hemisphere since the connection between the medial retinas and the cerebral hemispheres are crossed. Since a more positive PANAS score indicates more positive affect, we assign a value for the person's HEV according to the formula: LVF PANAS score–RVF PANAS. A positive score suggests that the right hemisphere has a more positive HEV. Research studies show that LVFS offers a good indication that the left and right cerebral hemispheres are generally associated with different emotional valences such that one hemisphere (either left or right) is associated with a more positive outlook on the world (positive hemispheric valence) and the other a more negative outlook on the world (negative hemispheric valence).

Figures 2A, 2B:
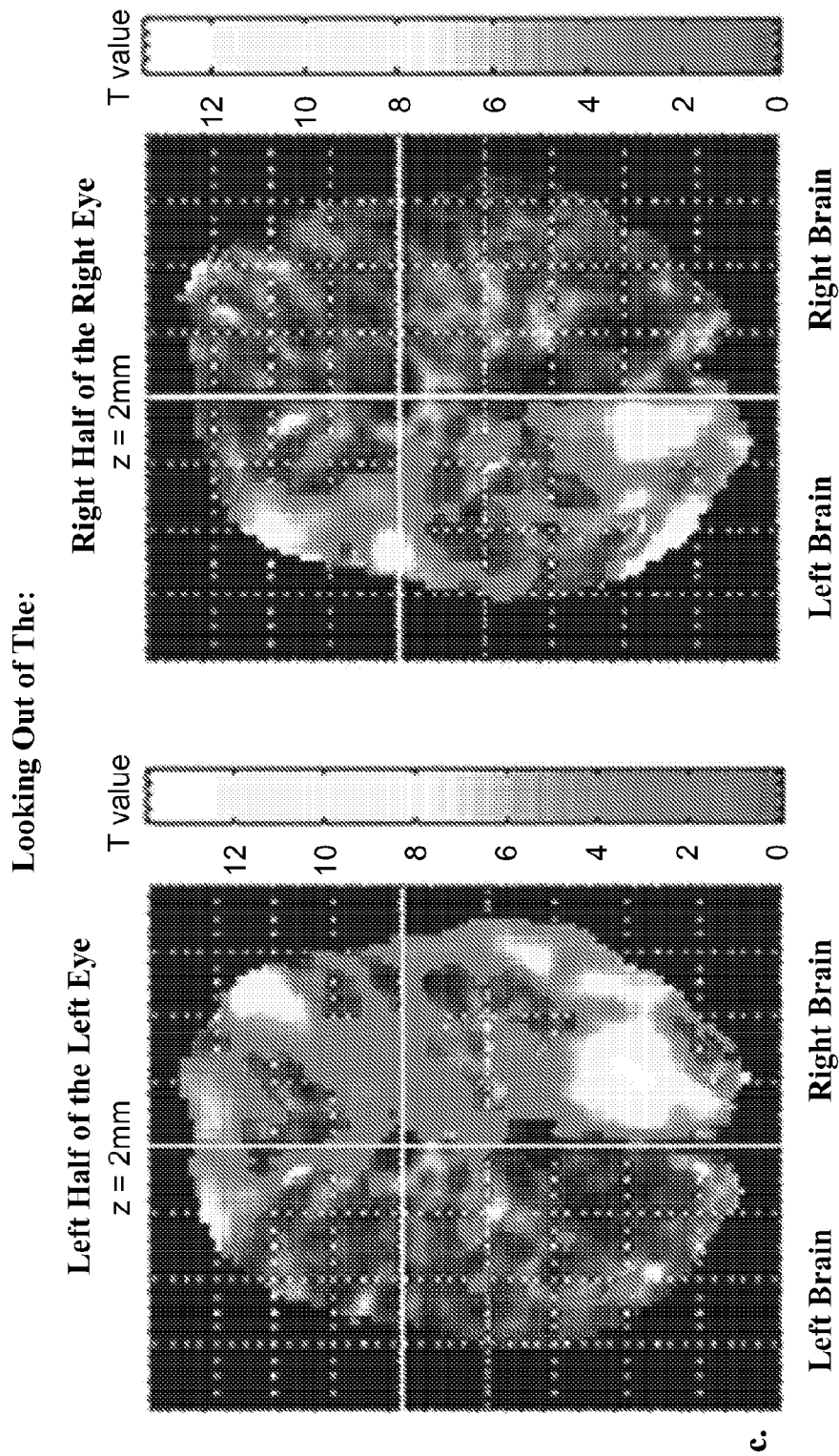
FIGS. 2A-2B show images of the brain having different activity by functional magnetic resonance imaging (fMRI) in the left and right cerebral hemispheres after looking out of the left or the right lateral visual field.

A person's personality and some of the person's psychological characteristics may be affected by which hemisphere, right or left hemisphere, dominates. The eyes are connected to the brain so that vision to the left side of a person goes first to the opposite (right) hemisphere and vision to the right side of a person goes first to the left hemisphere. One hemisphere can be stimulated over the other by restricting vision to a portion of the retina of an eye that is connected to a particular hemisphere of the brain. For instance, LVFS has been shown by fMRI to induce a very large increase in brain activity in the hemisphere opposite the visual field, when the subject looked out of the left visual field (LVF) and the right visual field (RVF). FIG. 2 shows images of the brain having different activity in the left and right cerebral hemispheres after looking out of the left and right lateral visual fields. FIG. 2A shows brain activity after looking out of the left half of the left eye. FIG. 2B shows brain activity after looking out of the right half of the right eye. As an example, a person looking out of one visual field might see another person as very critical of him and he might feel very critical of himself. Looking out the opposite visual field he is apt to see another person as quite approving of him and he is apt to see himself positively.

In an embodiment, the PANAS score may be used to determine which hemisphere of the brain to treat for a psychological disorder. Treating, or stimulating, one hemisphere of the brain at a time may cause certain changes in the psychological state of a person. These changes include, but are not limited to, a more positive outlook and a reduction in a negative outlook. In one embodiment, applying light over the upper side of the forehead (over the dorsolateral prefrontal cortex) will stimulate the hemisphere on that same side. In an embodiment, stimulating the brain in the medial pre-frontal cortex (stimulating transcranially on the forehead just above the eye on one side will inhibit the limbic system on that same side. In some embodiments, applying light on the forehead over the eye is likely to be emotionally inhibitory. In other embodiments, applying light over the upper side of the forehead (i.e., over the dorsolateral prefrontal cortex) over the hemisphere with a positive valence is likely to be helpful as would be treating over the medial pre-frontal cortex of the other hemisphere (with a more negative valence) to inhibit the limbic system of the hemisphere with a negative valence. With clinical practice, one could expect to improve this art by learning better locations and parameters for light treatments.

In an embodiment, diagnosing and treating one hemisphere of the brain may only cause changes in the psychological state of a person having a positive HEV. For example, treating the left hemisphere may benefit those patients who had a positive left hemispheric emotional valence (HEV), but not those with a negative left HEV. On the other hand, treating the right hemisphere may benefit those patients who had a positive right hemispheric emotional valence (HEV), but not those with a negative right HEV. In an embodiment, treating one hemisphere of the brain may only cause changes in the psychological state of person having a negative HEV. For example, treating the left hemisphere may benefit those patients who had a negative left hemispheric emotional valence (HEV), but not those with a positive left HEV. On the other hand, treating the right hemisphere may benefit those patients who had a negative right hemispheric emotional valence (HEV), but not those with a positive right HEV. In an embodiment, treating one hemisphere of the brain may cause changes in the psychological state of person having an either a positive HEV or a negative HEV. In an embodiment, diagnosis and treatment of a psychological disorder may be specific for each particular disorder. For example, treatment of anorexia may require treatment of the hemisphere with a positive HEV while treatment of insomnia may require treatment of the hemisphere with a negative HEV.

Figure 3:
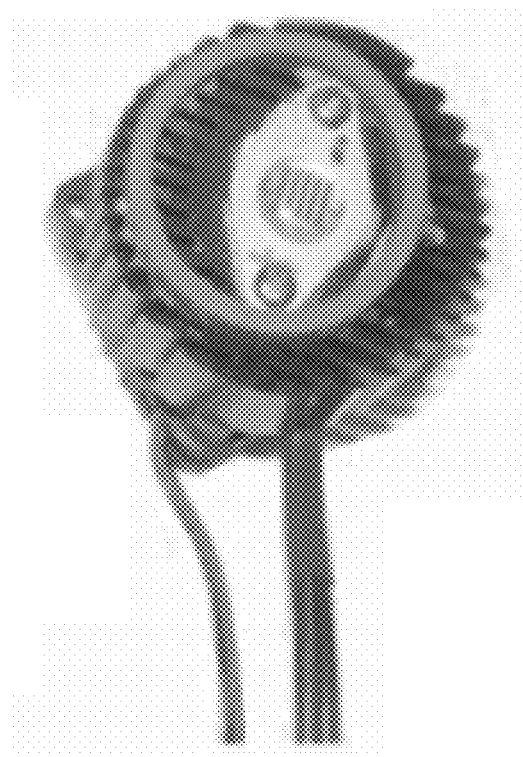
FIG. 3 shows NIR light being applied to the left side of the head using Photobiomodulation (PBM). The patches above the patient's eyebrows are connected to a commercial device for measuring cerebral blood flow in the front of the brain on the left and the right sides.
Figure 4:
FIG. 4 shows a close up of the NIR-PBM device of FIG. 3.
Figure 5:
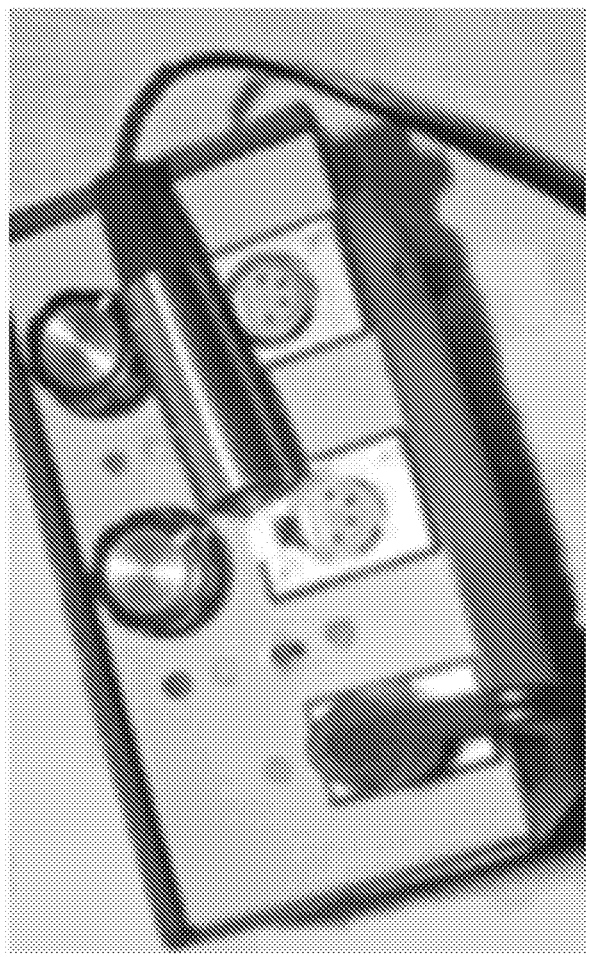
FIG. 5 shows a control unit of the NIR-PBM device of FIG. 3.

In an embodiment, the methods of the present disclosure may include using light energy to treat a hemisphere of the brain. In an embodiment, the light energy may include near infrared light (NIR). During this procedure, subjects can wear protective eyewear to prevent the light to be shined into their eyes. NIR light may, in an embodiment, be applied using Photobiomodulation (PBM) in the form of an LED, as shown in FIG. 3. FIG. 4 shows a close up of the PBM device. FIG. 5 shows a control unit of the PBM device. The control unit may contain a power supply. The power supply may be in the form of a battery or it may be connected to a power outlet. In an embodiment, the control unit may include at least one socket to connect with a LED. In an embodiment, one socket and one LED may be used to treat one location on a patient's head at a given time. In an embodiment, more than one LED can be used to treat more than one location on a patient's head at a given time. For example, in stroke patients, NIR may be used over the entire head. A knob is situated on the control unit to control the voltage to the LED. An increase in the voltage may be associated with an increase in the light being delivered.

In an embodiment, NIR light may be applied at a distance of about 0 to 1000 mm from the skin. In an embodiment, NIR light may be applied at a distance of about 4 mm from the skin. Placing the NIR light at a distance of about 4 mm from the skin at a power density of about 250 mW/cm$^2$ allows an amount of NIR light and intensity to be directed at a person's brain without causing harm to the brain during a 4-minute treatment at a given site. This dose may be safely delivered to other sites on the head in the same treatment setting. This dose could be increased as long as it is below the ANSI standard of about 320 mW/cm$^2$ on the skin at each site. It should be noted that the intensity of the NIR light increases as the NIR light approaches the skin and decreases in intensity by the square of the distance as the NIR light is moved away from the skin. One reason for choosing the distance of about 4 mm from the skin at a power density of about 250 mW/cm$^2$ is that the closer to the skin the more likely the LED will emit heat that cannot be dissipated by the heat sink and fan. If the patient can detect heat, placebo controlled studies may not be conducted as the patient may know whether the LED light was on or off. Also, the heat from the LED might cause the patient to feel pain the closer the LED is to the patient. Additionally, too much light, without heat, can cause damage to the skin. There is a conservative standard for the permissible amount of light (photons) at near infrared frequency of 810 nm, called the ANSI standard, as noted above, and studies with NIR light below that standard will not cause any harm to the patient.

During treatment, the light treatment device may be pulsed, or the light treatment may be continuously applied. In certain embodiments, the light treatment device may be combined with other types of treatments for an improved therapeutic effect. Treatment can include directing light through the scalp of the patient to a target area of the brain concurrently with applying an electromagnetic field to the brain. The light may be applied with a desired power density and with a desired electromagnetic field strength at the target area. In an embodiment, methods of treating a psychiatric disorder may include non-invasively irradiating at least a portion of a patient's brain with light energy having an efficacious power density and wavelength, sufficient to cause a neurotrophic effect and/or regulation of neurotransmitters. In another embodiment, methods of treating a psychiatric disorder may include non-invasively irradiating at least a portion of a patient's brain with light energy having an efficacious power density and wavelength, sufficient to cause a neurotrophic effect and/or regulation of neurotransmitters, and delivering the light energy for one or more treatment periods occurring over the course of at least one week, each treatment period having a duration of at least about 1 minute.

In an embodiment, the NIR light may be pulsed when applied to the skin. Pulsing the NIR light can allow the use of a more intense light and yet remain below the ANSI standard. Pulsing the NIR light may be used to entrain the brain and thereby affect the state of the brain. A faster entrainment can increase brain activity, and a slower entrainment can decrease brain activity.

The light output may be continuously applied at about 250 mW/cm$^2$ at a wavelength of about 810 nm with a full width half maximum of about 40 nm. In an embodiment, the NIR light may be directed at a person's brain for about 4 minutes (total delivered fluence per spot of 60 J/cm$^2$). In an embodiment, the procedure with the NIR light may be repeated at at least one other site on the forehead. In an embodiment, the NIR light may penetrate the dura, or the outermost of the three layers of the meninges surrounding the brain, at about 3.7%. In accordance with a penetration of about 3.7%, approximately 2.1 J/cm$^2$ of fluence is delivered to each of the treated areas of the brain. It should be noted that the level of light exposure is below the ANSI standard of 320 mW/cm$^2$. The level of light exposure either to the skin (power density of 250 mW/cm$^2$ and total fluence of 60 J/cm$^2$), to the surface of the brain (power density of 9.5 mW/cm$^2$ and total fluence of 2.1 J/cm$^2$) and to each of the 2 treated areas of the forehead poses no significant risk to the skin or the brain. It should be noted that while described above with a specific frequency, the invention of the present disclosure could also use a frequency from about 300 nm to about 1500 nm. Furthermore, the present invention can use any source of light, whether low level laser or LED, so long as its duration and intensity are below the ANSI standard of 320 mW/cm$^2$ on the skin.

The methods of the present disclosure may affect blood flow within the brain. Blood flow in the brain can be measured in left and right frontal poles by NIRS, by a blood flow monitoring device, such as a Somanetics INVOS system, modified by Somanetics to provide total hemoglobin (cHb). In an embodiment, the blood flow monitoring device uses a low power NIR LED. The blood flow monitoring device has no effect on the brain. The blood flow monitoring device measures the amount of blood in the brain once a second. In an embodiment, the Somanetics devices measures oxy- and deoxy-hemoglobin. The blood flow monitoring device poses no harm or discomfort to subjects and allows subjects to have relatively free movement. The blood flow monitoring device can be used to monitor cHb in the left and right frontal poles during PBM. Since the PBM used in an embodiment of the present disclosure is a continuous wave, the light from the PBM is not detected by this NIRS device because it has a proprietary mechanism for excluding continuous light so that sunlight does not affect the device's pulsed photon emitter. It should be noted that the Somanetics device is FDA approved, is commercially available, and is used throughout the world in hospital settings to monitor cerebral perfusion.

Figure 6:
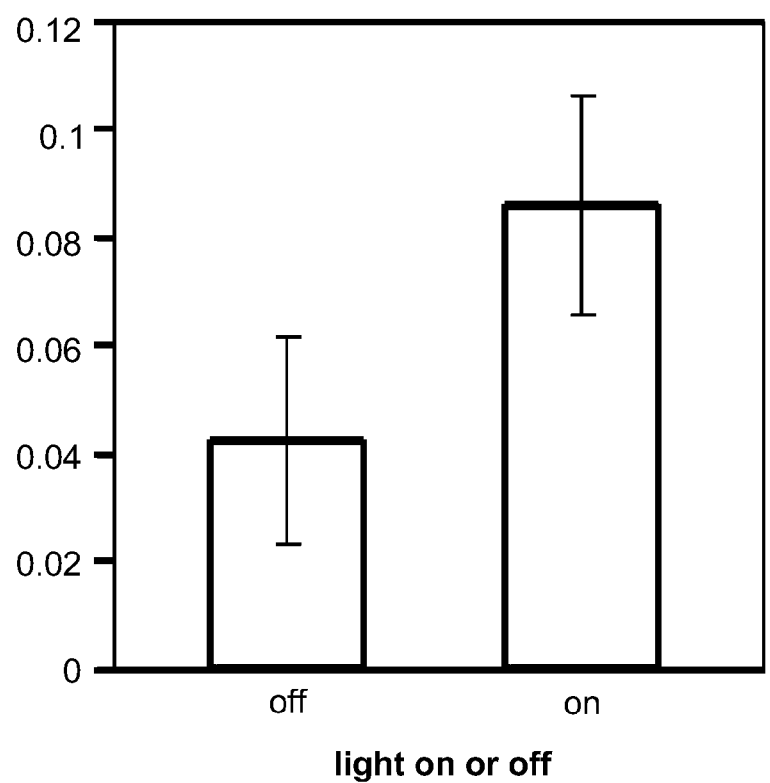
FIG. 6 shows that there was an increase in cerebral blood flow when the NIR light was on compared to when it was off.
Figure 7:
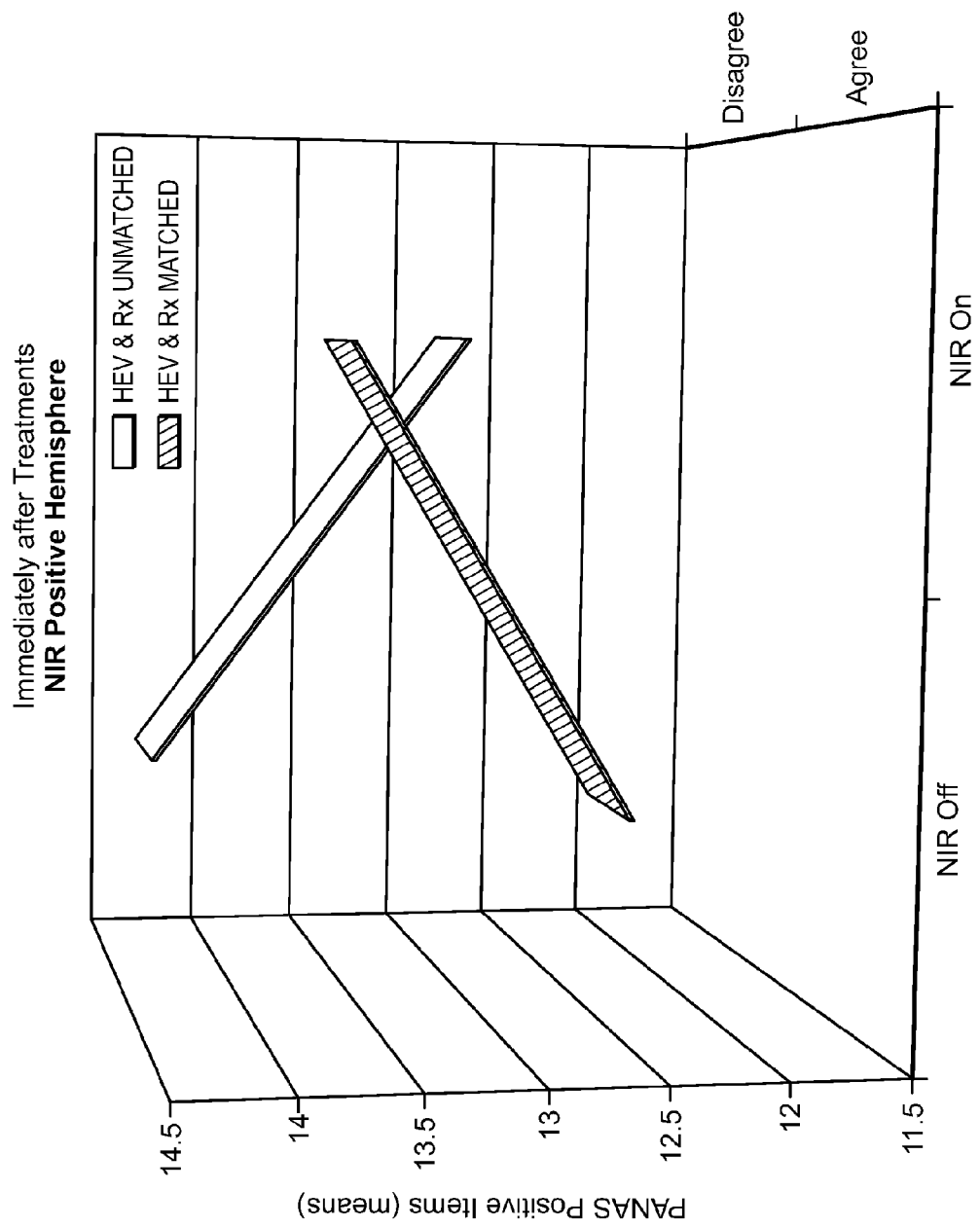
FIG. 7 shows that after the NIR treatment, there was an increase in positive affect when the brain hemisphere with a positive emotional valence was treated (matched treatment and hemisphere), but a decrease in positive affect when the brain hemisphere with a negative emotional valence was treated (unmatched).

In an embodiment, cHb can be measured by NIRS during treatments at at least one point. In an embodiment, there may be a correlation between NIR and improved cHb and mood. For example, there may be greater total (left plus right) cHb during NIR on versus off as shown in FIG. 6. FIG. 7 shows that there was a significantly more positive affect when the hemisphere with a positive HEV was treated with NIR-PBM and a significantly more negative affect after a hemisphere with a negative HEV was treated. In FIG. 7, "matched" refers to treating the hemisphere with a positive HEV and "unmatched" refers to treating the hemisphere with a negative HEV. PANAS scores declined when the negative hemisphere was treated. Thus, in a blind, placebo-controlled secondary study, the PANAS scores improved on the PANAS items, following NIR treatments to the hemisphere with a more positive HEV. The PANAS scores correlated very highly with the HEV values times agreement (1) or disagreement (−1) with the side treated.

Figure 8:
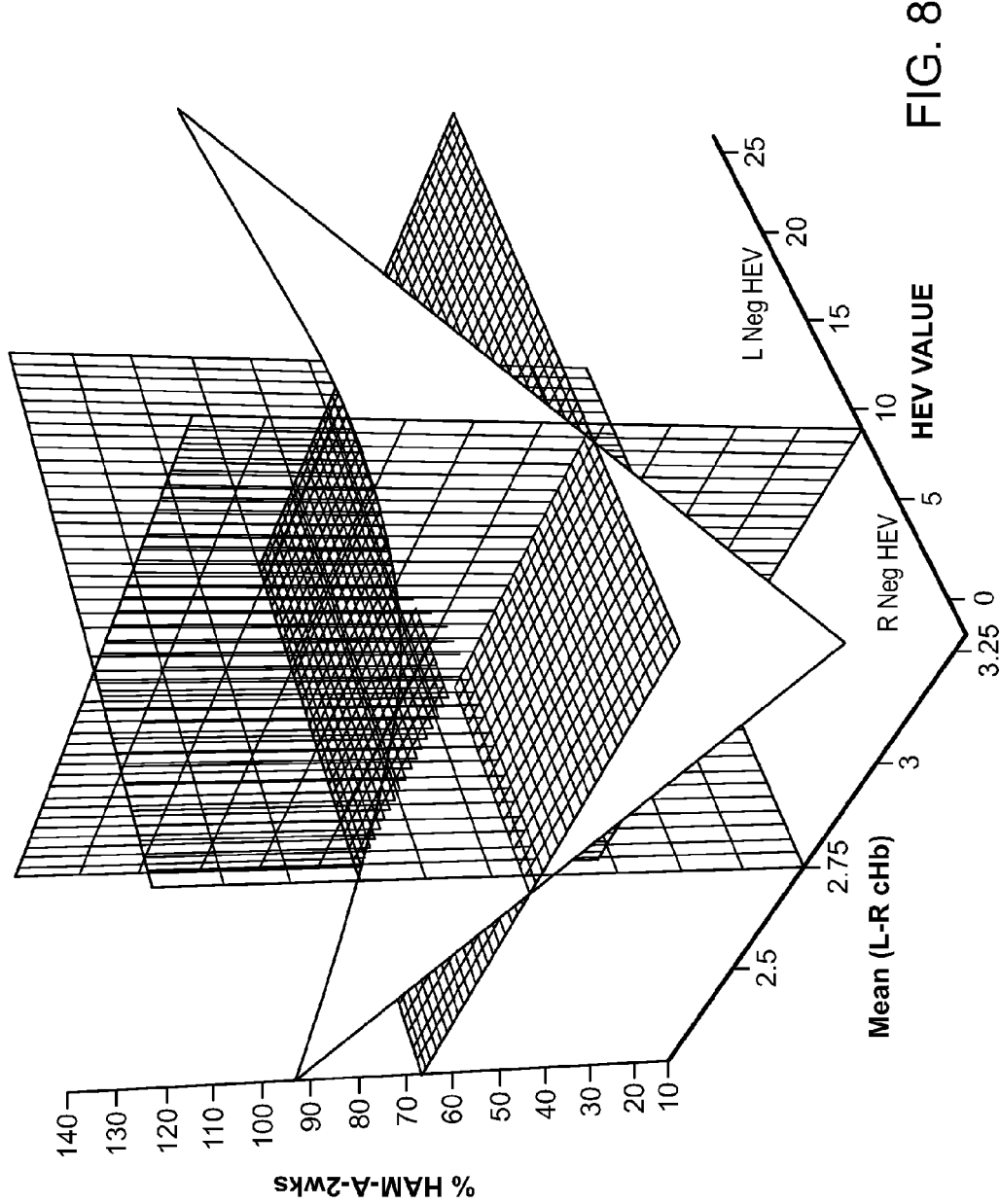
FIG. 8 shows that at 2-weeks post treatment, a decrease in anxiety (as measured by the Hamilton Anxiety Rating Scale) was related to the patient's baseline hemispheric emotional valence (HEV) and cerebral blood flow. Those patients with a left negative HEV and an increase in right frontal CBF had less anxiety, as did those patients with a right negative HEV and an increase in left frontal CBF.

The increase in cHb with NIR suggests that the NIR treatment is affecting the brain. The improvement in PANAS immediately following the treatment may indicate that this effect on the brain likely relates to the alterations in affect. FIG. 8 shows that at 2-weeks post treatment, a decrease in anxiety (as measured by the Hamilton Anxiety Rating Scale) was related to the patient's baseline HEV and cerebral blood flow (CBF). In an embodiment, patients with a left negative HEV and an increase in right frontal CBF had less anxiety. In an embodiment, patients with a right negative HEV and an increase in left frontal CBF had less anxiety. Thus, patients who had an increase in blood flow in their positive hemisphere did better at 2-weeks post treatment. If a person has a negative side, increasing the blood flow on the opposite side can have a beneficial effect at 2-weeks post treatment. The fact that the outcomes at 2-weeks were dependent in regression models on the baseline HEV value is consistent with the fact that right hemisphere is often associated with a positive HEV (in opposition to the popular notion that negative affect and/or cognition are associated always with the right hemisphere) and that knowing a patient's HEV can enlighten data reduction and guide treatment. Cerebral blood flow correlates with brain activity in the front of the brain. Patients with a negative right HEV and an increased left CBF and patients with a negative left HEV and an increased right CBF may have significantly better outcomes in terms of their Hamilton Anxiety Rating Scale scores at 2-weeks post NIR treatment.

Several theories may help explain the possible correlation between NIR light and improved cHb and mood. NIR light is known to increase and/or stimulate mitochondrial ATP and nerve growth factors. This may be because the energy from the NIR light may be absorbed by the mitochondria, which are the energy production centers of the brain. Increasing and/or stimulating mitochondria and mitochondrial ATP may help stimulate the positive neural circuits or inhibit the negative neural circuits. It is further known that light therapies may promote wound healing or reduce the damage from strokes or heart attacks. Such studies were conducted in rats and rabbits.

It should be noted that patients who were treated bilaterally with the methods of the present disclosure experienced a remission of anxieties at a rate of about seventy percent. Remission refers to the state of absence of disease activity in patients with a chronic illness. Remission is measured using a rating scale where a score of greater than fifteen on the rating scale correlates to having an anxiety disorder and a score of ten or less on the rating scale correlates to being in remission and no longer manifesting an abnormal level of anxiety. Compared to other treatments, a remission rate of about seventy percent is very high. On the Hamilton Depression Scale there was an average percent decrease (percent less depression) of 54% 2-weeks after the single treatment, and on the Hamilton Anxiety Rating Scale, at 2-weeks post treatment, there was a percent decrease of 63%. These also compare well with other treatments. For example, studies have found that after 29 patients with an anxiety disorder were treated with cognitive behavioral therapy for 30 weeks, those 29 patients achieved a 51% reduction on the Hamilton Anxiety Rating Scale at the end of the treatment. In addition, studies have found that after 28 patients having an anxiety disorder were treated with short-term psychodynamic psychotherapy for 30 weeks, those 28 patients achieved a 43% reduction on this anxiety rating scale at the end of the treatment. In an embodiment, the methods of the present disclosure treats patients with light therapy for a total of about 8 minutes, is pain free, and without any observed side effects, and is generally inexpensive.

According to aspects illustrated herein, there is provided a method for treating psychiatric disorders using light energy, including determining which hemisphere of the brain requires treatment using lateral visual field stimulation (LVFS) and applying light energy to the hemisphere of the brain to treat the psychiatric disorder other than depression. In an embodiment, light energy may include near infrared light (NIR). The methods of the present disclosure may be used to treat a variety of psychiatric disorders.

According to aspects illustrated herein, there is provided a method for treating a psychiatric disorder in a patient, including measuring a left hemispheric emotional valence and a right hemispheric emotional valence for a left hemisphere of the brain and a right hemisphere of the brain using a lateral visual field stimulation test; determining which hemisphere of the brain needs treatment; and applying light energy to the hemisphere of the brain to treat the psychiatric disorder co-morbid with depression.

According to aspects illustrated herein, there is provided a method for treating a psychiatric disorder in a patient, including measuring a left hemispheric emotional valence for a left hemisphere of the brain and a right hemispheric emotional valence for a right hemisphere of the brain using a lateral visual field stimulation test; determining the hemisphere of the brain in need of treatment; and applying light energy to the hemisphere of the brain to treat the psychiatric disorder co-morbid with depression.

According to aspects illustrated herein, there is provided a method for treating psychiatric disorders using light energy including determining which hemisphere of the brain has a more positive affect using lateral visual field stimulation (LVFS) and applying light energy to the hemisphere with the more positive affect. In an embodiment, light energy may include near infrared light (NIR). The methods of the present disclosure may be used to treat a variety of psychiatric disorders.

According to aspects illustrated herein, there is provided a method for treating psychiatric disorders using light energy including determining which hemisphere of the brain has a more negative affect using lateral visual field stimulation (LVFS) and applying light energy to the hemisphere with the more negative affect to improve its functioning. In an embodiment, light energy may include near infrared light (NIR). The methods of the present disclosure may be used to treat a variety of psychiatric disorders.

According to aspects illustrated herein, there is provided a method for treating psychiatric disorders using light energy including determining which hemisphere of the brain has a more positive and negative affect using lateral visual field stimulation (LVFS); applying light energy to the hemisphere with the more positive affect; and applying light energy to the hemisphere with the more negative effect. In an embodiment, if both hemispheres have about equal levels of positive or negative affects, both hemispheres may benefit from the light energy. In an embodiment, light energy may include near infrared light (NIR). The methods of the present disclosure may be used to treat a variety of psychiatric disorders.

According to aspects illustrated herein, there is provided a method for treating psychiatric disorders using light energy including determining which hemisphere of the brain has a more negative affect using lateral visual field stimulation (LVFS); applying light energy to the hemisphere with the more negative affect; and increasing cerebral blood flow in the opposing hemisphere. In an embodiment, light energy may include near infrared light (NIR). The methods of the present disclosure may be used to treat a variety of psychiatric disorders.

According to aspects illustrated herein, there is provided method for treating a patient, including determining which portion of the brain of the patient requires treatment; and applying light energy to the portion to treat the patient. The light might be applied bilaterally over the left and the right dorsolateral pre-frontal coracles. In an embodiment, the treatment may be used to treat depression. In another embodiment, the treatment may be used to improve the well-being of the patient.

According to aspects illustrated herein, there is provided a method for treating a patient, including determining which portion of the brain needs treatment; and applying light energy to the portion of the brain to treat the patient. In an embodiment, the treatment may be used to treat depression. In an embodiment, the treatment may be used to cause an improvement in the well-being of the patient.

According to aspects illustrated herein, there is provided a method for treating a psychiatric disorder in a patient including applying light energy to a brain to treat the psychiatric disorder.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art.

What is claimed is:

1. A method for enhancing positive outlook of a person with hemispheric asymmetry comprising identifying a person with a deficient positive outlook in need of enhancement;

measuring a left hemispheric emotional valence for a left hemisphere of a brain of the person and a right hemispheric emotional valence for a right hemisphere of the brain of the person to identify hemispheric asymmetry;

determining which hemisphere of the brain of the person with hemispheric asymmetry has a more positive valence, and which hemisphere of the brain has a more negative valence; and transcranially applying light energy having a wavelength of between 300 nm to 1500 nm and a power density at the scalp of up to 320 mW/cm$^2$ to the brain of said person with the deficient positive outlook with hemispheric asymmetry, wherein the light energy is transcranially applied to the lateral forehead to activate the underlying cortex of the brain hemisphere with a more positive valence for a period of at least four minutes, such that the positive outlook of the person is enhanced.

2. The method of claim 1, wherein the positive outlook that is enhanced is psychological well-being.

3. The method of claim 1 wherein the light energy has a wavelength of 810 nm.

4. The method of claim 2, wherein the light energy has a wavelength of 810 nm.

5. The method of claim 2, wherein the enhanced psychological well-being is selected from emotional outlook, cognitive outlook, or motivational outlook.

6. The method of claim 2, wherein the enhanced psychological well-being comprises improvement in appreciation for life, self, work, or personal relationships.

7. The method of claim 2, wherein the enhanced psychological well-being comprises prospering in: life, work, or interpersonal relationships.

\* \* \* \* \*